United States Patent [19]

Kozlow

[11] 4,264,008
[45] Apr. 28, 1981

[54] ADHESIVE BANDAGE AND PACKAGE

[76] Inventor: William J. Kozlow, 11110 Rumford Ct., Pinellas Park, Fla. 33565

[21] Appl. No.: 853,188

[22] Filed: Nov. 21, 1977

[51] Int. Cl.³ .................. A61B 19/02; A61B 17/06
[52] U.S. Cl. .................................................. 206/441
[58] Field of Search .............. 206/441, 411, 412, 63.3, 206/438

[56] References Cited

U.S. PATENT DOCUMENTS

| | | | |
|---|---|---|---|
| 2,946,435 | 7/1960 | Schladermundt et al. | 206/441 |
| 2,969,144 | 1/1961 | Zackheim | 206/441 |
| 2,969,145 | 1/1961 | Hannauer, Jr. | 206/441 |
| 3,032,181 | 5/1962 | Hutter et al. | 206/411 |
| 3,313,405 | 4/1967 | Blackford | 206/441 |
| 3,618,756 | 11/1971 | Trewella | 206/438 |
| 3,855,052 | 12/1974 | Mestetsky | 206/411 |
| 3,967,728 | 7/1976 | Gordon et al. | 206/438 |

Primary Examiner—William T. Dixson, Jr.
Attorney, Agent, or Firm—Martha G. Pugh

[57] ABSTRACT

A particular feature of the invention is that the gas-pervious package is internally sealed together only in those areas immediately adjacent the peripheral portions, leaving an unsealed space internally surrounding the bandages in the package to facilitate sterilization.

An adhesive bandage and package is provided wherein the package portion of the bandage serves as means by which the bandage may be applied to the wound without affecting sterility. More precisely, the adhesive bandage, having a backing, and a pad with a facing, is folded with the uncoated face of the backing back to back and is covered by a suitable covering material that is heat, pressure, or ultrasonic sealed on the four sides parallel to the edges of the cover. One portion of the cover extends beyond the seal lines and serves as means for opening and applying the bandage. In another embodiment the opening means is a tear area positioned between the pad and the end of the package.

12 Claims, 12 Drawing Figures 13  15 16 21 22

13  15 16 21 22

ADHESIVE BANDAGE AND PACKAGE

BACKGROUND OF THE INVENTION

The adhesive bandages of prior art are packaged in packages which are separate from the bandages. They are usually equipped with a tearstring or some other means for opening the package. The package serves primarily to maintain sterility of the bandage. Upon removal of the bandage from the package one is to hold onto the extended portions of a release coated paper or plastic material covering the face and the adhesive portions of the bandage in order to apply the same to the wound.

My invention obviates the use of the separate release coated paper or plastic material that is used to apply the adhesive bandage thus providing an economic advantage. It also eliminates the unnecessary separate handling of the adhesive bandage thereby minimizing the chance of contamination, and the adhesive bandage is easier and faster to apply because the package is used as the means to apply the adhesive bandage.

PURPOSE OF THE INVENTION

The purpose of my invention is to provide an adhesive bandage and package in which conventionally used means to apply the adhesive bandage to a wound are eliminated, sterility maintained, and ease of handling is insured. Another purpose of my invention is to reduce the amount of material used in an adhesive bandage and package and thus obtain an economic gain.

SUMMARY OF THE INVENTION

The purposes and objectives of the present invention are accomplished in an adhesive bandage and package wherein the adhesive bandage is composed of a backing of a suitable material on one side of which, and about centrally positioned, is a pad; and the remaining area of the same side of the backing is coated with a pressure sensitive adhesive, the bandage is folded on a transverse axis in such manner that the two sections of the uncoated face of the backing face each other and the coated two sections and pad are facing outward. There is placed over the bandage a plastic or a release-coated paper or foil, completely covering the adhesive portions and pad portion of the bandage and overlapping all edges with a greater portion extending outward from the fold-line axis. Said cover material is then heat, pressure or ultrasonic sealed beyond the periphery of the bandage and parallel to the cover edges. The portion of the cover beyond the seal that is adjacent to the bandage fold serves as the means to hold and open the package, to apply the bandage. The purposes and objectives accomplished will be more readily understood from the detailed description that follows.

DETAILED DESCRIPTION OF THE DRAWINGS

Figure 1:
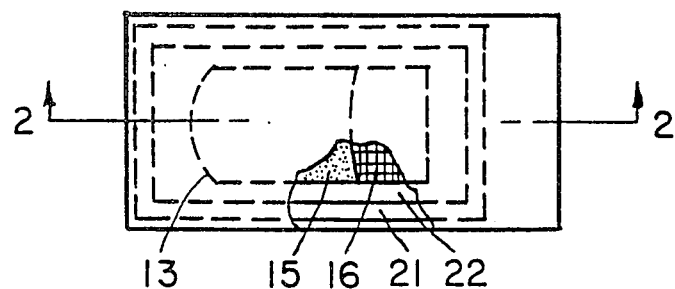
FIG. 1 is a plan view of the adhesive bandage and package. The adhesive bandage is folded across its width exactly in half with the backing back to back and the adhesive coating and the bandage pad facing out. The bandage is covered with two pieces of a covering material of substantially the same shape as the bandage but its dimensions are larger so that it extends somewhat beyond the edges of the folded bandage. The package is sealed on four sides parallel to the four edges of the folded adhesive bandage. There is a space between the inside edge of the package seal and the four edges of the adhesive bandage. The seal is formed by heat and pressure, pressure or ultrasonics. The package is longer on one end beyond the package seal thus forming the package peel tabs. The peel tabs have a straight shape and are on the end of the package nearest to the fold on the adhesive bandage.

Referring to FIGS. 1, 2, 3 and 4 the adhesive bandage 13 has a perforated plastic backing 14, that is entirely coated on one face with a pressure sensitive adhesive 15. The bottom face of an absorbant pad 16 is stuck onto the adhesive 15 in the center of the adhesive face. The absorbant pad 16 has a wound release facing.

The adhesive bandage 13 is folded with the adhesive 15 and the absorbant pad 16 facing out and the uncoated face of the backing 14 is back to back. The fold 17 is across the bandage width at its center as in FIGS. 1 and 2 or the fold 17 could be at any distance from one end of the bandage up to and including the center as in FIGS. 3 and 4.

Figure 3:
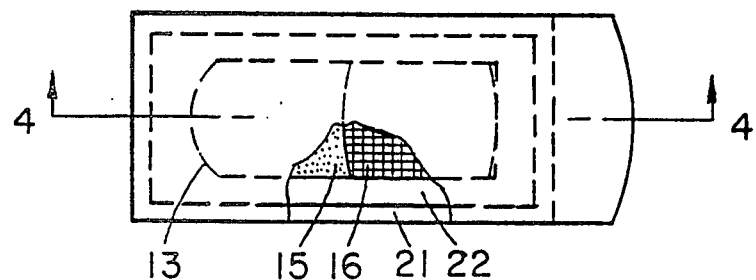
FIG. 3 is a plan view of another embodiment of the present invention of the adhesive bandage and package. The materials and construction are the same as FIG. 1 except the adhesive bandage is folded across its width with the fold at any distance from one end of the bandage up to the center of the bandage; and the package peel tabs have a curved shape.
Figure 4:
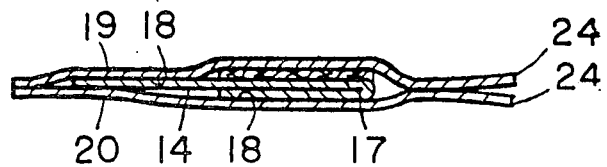
FIG. 4 is a cross section of the adhesive bandage and package shown in FIG. 3 taken along line 4—4.
Figure 5:
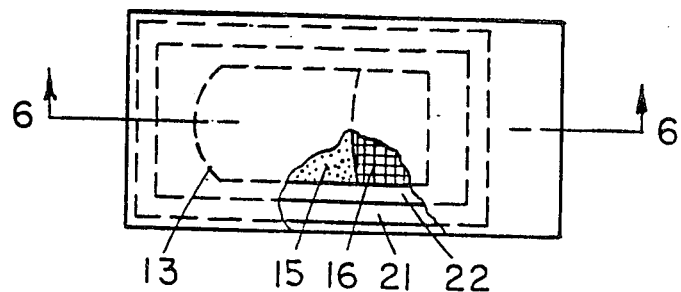
FIG. 5 is a plan view of the adhesive bandage and package. The adhesive bandage is folded across its width exactly in half with the backing back to back and the adhesive coating and the bandage pad facing out. The bandage is covered with one piece of a covering material folded to make both sides of the package. The covering material is substantially the same shape as the bandage but its dimensions are larger so that it extends somewhat beyond the edges of the folded bandage. The package is sealed on four sides parallel to the four edges of the folded adhesive bandage. There is a space between the inside edge of the package seal and the four edges of the adhesive bandage. The seal is formed by heat and pressure, pressure or ultrasonics. The package is longer on one end beyond the package seal thus forming the package peel tabs. The peel tabs have a straight shape and are on the end of the package nearest to the fold on the adhesive bandage and the fold on the package is on the end of the package furthest from the fold on the adhesive bandage.
Figure 6:
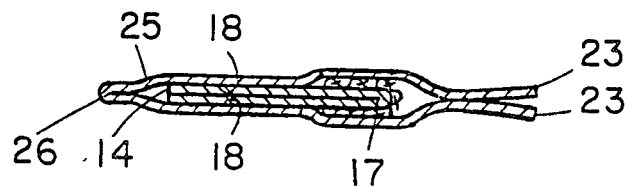
FIG. 6 is a cross section of the adhesive bandage and package shown in FIG. 5 taken along line 6—6.

The package in FIGS. 1 and 3 is made from two pieces of plastic or from paper, foil or similiar material that is coated on one face with plastic or silicone. The coated face 18 on package side 19 is placed on the adhesive face 15 on one side of the folded adhesive bandage 13. The coated face 18 of package side 20 is placed on the adhesive face 15 on the opposite side of the folded adhesive bandage.

The two pieces of the package 19 and 20 are sealed together by heat and pressure, pressure or ultrasonics. The package seal 21 is parallel to the four edges of the package and the four edges of the folded adhesive bandage 13. There is a space 22 between the inner edge of the package seal 21 and the four edges of the folded adhesive bandage 13.

Package sides 19 and 20 extend on one end of the package beyond the outside edge of the package seal 21 to form the package peel tabs. The peel tabs have a straight shape 23 or a curved shape 24. The package peel tabs 23 or 24 are on the end of the package nearest the fold 17 on the adhesive bandage 13.

In another embodiment of the invention as illustrated in FIGS. 5, 6, 7 and 8, the package 25 is formed from one piece of plastic, or from one piece of paper, foil or similar material that is coated on one face 18 with plastic or silicone and folded 26 across its width to form both sides of the package 25 with the coated face 18 on the inside. The coated face 18 of the package 25 is placed on the adhesive coated faces 15 on the folded adhesive bandage 13. The folded end 26 on the package 25 is on the end of the package furthest from the fold 17 on the adhesive bandage 13. The package 25 is sealed together by heat and pressure, pressure or ultrasonics. The package seal 21 is parallel to the four edges of the package and the four edges of the folded adhesive bandage 13. There is a space 22 between the inner edge of the package seal 21 and the four edges of the folded adhesive bandage 13.

Figure 2:
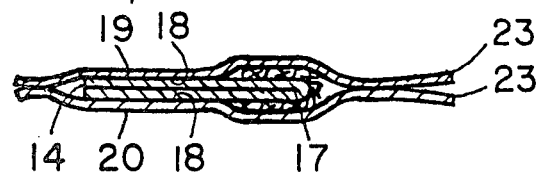
FIG. 2 is a cross section of the adhesive bandage and package shown in FIG. 1 taken along line 2—2.
Figure 9:
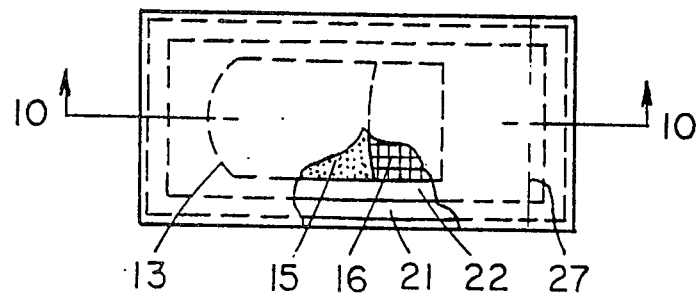
FIG. 9 is a plan view of the adhesive bandage and package. The adhesive bandage is folded across its width exactly in half with the backing back to back and the adhesive coating and the bandage pad facing out. The bandage is covered with two pieces of a covering material of substantially the same shape as the bandage but its dimensions are larger so that it extends somewhat beyond the edges of the folded bandage. The package is sealed on four sides parallel to the four edges of the folded adhesive bandage. The seal is formed by heat and pressure, pressure or ultrasonics. There is a space between the inside edge of the package seal and the four edges of the adhesive bandage. There is on one end of the package a greater space between the seal and the fold on the adhesive bandage. This package has no peel tabs. To open the package and to apply the adhesive bandage to a wound, this end of the package is torn across its width just inside the heat seal. The small end is discarded. The remaining package is opened at the tear end by pulling it apart.
Figure 10:
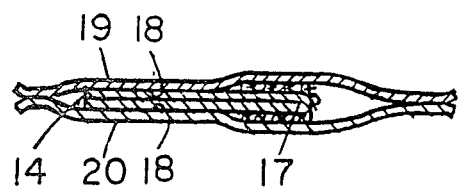
FIG. 10 is a cross section of the adhesive bandage and package shown in FIG. 9 taken along line 10—10.

The adhesive bandage and package illustrated in FIGS. 9 and 10 has the same construction and the same materials as the adhesive bandage and package illustrated in FIGS. 1 and 2 except there are no package peel tabs and there is a greater space 22 between the fold end 17 on the adhesive bandage and the inner edge of the package seal 21. The package tear line 27 is in the extended space 22 parallel and close to the inside edge of the package end seal 21.

Figure 7:
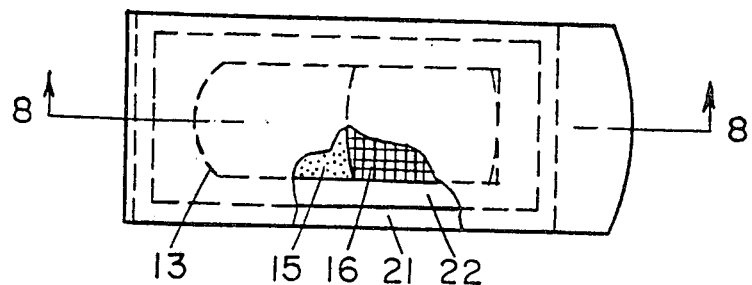
FIG. 7 is a plan view of another embodiment of the present invention of the adhesive bandage and package. The materials and construction are the same as FIG. 5 except the adhesive bandage is folded across its width with the fold at any distance from one end of the bandage up to the center of the bandage; and the package peel tabs have a curved shape.
Figure 8:
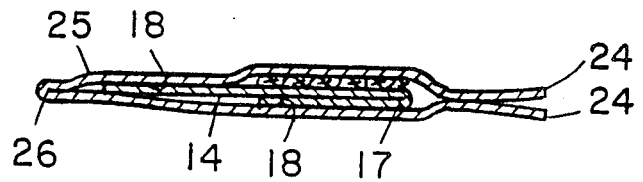
FIG. 8 is a cross section of the adhesive bandage and package shown in FIG. 7 taken along line 8—8.
Figure 11:
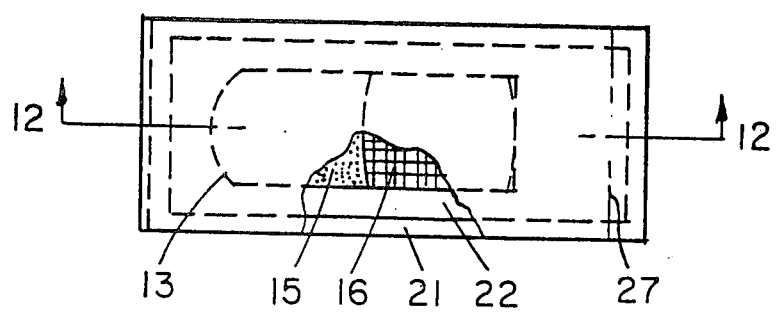
FIG. 11 is a plan view of another embodiment of the present invention of the adhesive bandage and package. The adhesive bandage is folded across its width with the fold at any distance from one end of the bandage up to the center of the bandage with the backing back to back and the adhesive coating and bandage pad facing out. The bandage is covered with one piece of a covering material folded to make both sides of the package. The covering material is substantially the same shape as the bandage but its dimensions are larger so that it extends somewhat beyond the edges of the folded bandage. The package is sealed on four sides parallel to the edges of the folded adhesive bandage. The seal is formed by heat and pressure, pressure or ultrasonics. There is a space between the inside edge of the package seal and the four edges of the adhesive bandage. There is on one end of the package a greater space between the seal and the fold on the adhesive bandage. This package has no peel tabs. To open the package and to apply the adhesive bandage to the wound, this end of the package is torn across its width just inside the heat seal. The small end is discarded. The remaining package is opened at the tear end by pulling it apart. The fold on the package is opposite the tear end of the package.
Figure 12:
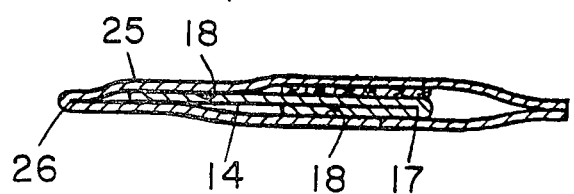
FIG. 12 is a cross section of the adhesive bandage and package shown in FIG. 11 taken along line 12—12.

The adhesive bandage and package illustrated in FIGS. 11 and 12 has the same construction and the same materials as the adhesive bandage and package illustrated in FIGS. 7 and 8 except that there are no package peel tabs and there is a greater space 22 between the fold end 17 on the adhesive bandage and the inner edge of the package seal 21. The package tear line 27 is in the extended space 22 parallel and close to the inside edge of the package end seal 21.

The adhesive bandage and package FIGS. 1 thru 12 for sterilization by steam or gas has a paper package and there is no coating on both inside faces of the package in the area covering the space 22 between the edges of the adhesive bandage 13 and the inner edge of the package seal 21.

The package seal 21 in FIGS. 1 thru 12 is formed by heat and pressure or ultrasonics on plastic packages or packages that are coated on the inside in the seal area 21 with plastic.

The package seal 21 in FIGS. 1 thru 12 is formed by pressure on all packages coated on the inside in the seal area 21 with a pressure sensitive adhesive.

DESCRIPTION OF MATERIALS OF CONSTRUCTION

The adhesive bandage is made from materials customarily used to make an adhesive bandage. More specifically the adhesive bandage of the present invention can be made of materials as follows: In a conventionally used bandage there are three essential components: a backing, adhesive, and a pad for contacting the wound. The backing is made from a soft plastic and is perforated throughout. The adhesive is a pressure sensitive material composed of a rubber or plastic compound; and the bandage pad is made from plastic foam, paper, cotton or gauze with or without a non-adherant plastic material on the top face for wound release.

The package or covering utilizes materials customarily used in making adhesive bandages and their wrappers. The package is made from paper or foil, with a plastic or silicone coating on one side or from plastic. A package with a coating of a pressure sensitive adhesive compound of rubber or plastic in the seal area is closed by pressure and a package with a plastic coating in the seal area is closed by heat and pressure or ultrasonics.

What is claimed is:

1. A combination comprising:
   an adhesive bandage having a backing element with a pressure-sensitive coating on one side only, and a pad centrally positioned on the coated side thereof;
   said adhesive bandage being folded on its transverse axis so that at least a portion of the uncoated surfaces of said backing element are in back-to-back relation;
   a gas-pervious package covering said folded adhesive bandage and constructed for in situ sterilization of said bandage in said package, said package being similar in shape but exceeding the dimensions of said folded adhesive bandage so that the edges of said package extend substantially beyond the edges of said folded adhesive bandage, the inside surfaces of said package being internally sealed together only in those areas immediately adjacent the peripheral portions thereof leaving an unsealed space internally in said package between said peripheral portions and said adhesive bandage, wherein said unsealed space surrounds said adhesive bandage;
   said gas-pervious package being coated with plastic or elastomer on the side facing the pressure-sensitive coating of said backing element only in those areas where said package contacts said adhesive bandage, and in the seal areas immediately adjacent the peripheral portions of said package, whereby said package is designed to permit the penetration of sterilizing steam or gas into said package through the uncoated portions, and into said unsealed space between said adhesive bandage and the seal areas adjacent the peripheral portions of said package.

2. The combination in accordance with claim 1 wherein said gas-pervious package comprises paper at least partially coated with a silicone coating on the side facing the pressure-sensitive coating of said backing element.

3. The combination in accordance with claim 1 wherein said gas-pervious package comprises paper at least partially coated with plastic on the side facing the pressure-sensitive coating of said backing element.

4. The combination in accordance with claim 1 wherein said gas-pervious package comprises paper at least partially coated with a pressure-sensitive adhesive on the side facing the pressure-sensitive coating of said backing element.

5. The combination in accordance with claim 1 wherein the adhesive bandage is folded to form a fold along a transverse axis thereof equidistant from the ends.

6. The combination in accordance with claim 1 wherein the adhesive bandage is folded to form a fold along a transverse axis at a distance not equidistant from the ends.

7. The combination in accordance with claim 1 wherein said gas-pervious package comprises two substantially symmetrical pieces having their coated inside surfaces in substantially face-to-face relation, being sealed together only in the areas immediately adjacent the peripheral portions thereof, the two end portions of said pieces being extended away from the fold axis of said bandage to form a pair of peel tabs.

8. The combination in accordance with claim 1 wherein said package comprises one piece folded with the coated inside surfaces thereof in face-to-face relation along a transverse fold axis disposed at the opposite end of the fold axis of said bandage, being sealed together only in the area immediately adjacent the peripheral portions of said package, the end portions extended away from the fold axis of said bandage to form a pair of peel tabs.

9. The combination in accordance with claim 1 wherein the end of said package extends out from the fold axis of said bandage and includes a tear area across said open space adjacent a sealed peripheral portion of said package.

10. The method of packaging an adhesive bandage in a package constructed for in situ sterilization, said package comprising a backing element having a pressure-sensitive coating on one side only, on which a pad is centrally disposed, the steps of
    folding said bandage transversely so that at least a portion of the uncoated surfaces of said backing element are in back-to-back relation;
    covering said adhesive bandage with a gas-pervious package which is similar in shape but which exceeds the dimensions of said folded adhesive bandage so that the edges of said package extend substantially beyond the edges of said folded adhesive bandage; and
    sealing together the internal surfaces of said package only in those areas immediately adjacent to the peripheral portions thereof leaving an unsealed space internally in said package between said peripheral portions and said adhesive bandage, wherein said unsealed space completely surrounds said adhesive bandage.

11. The method in accordance with claim 10 which includes the steps of:
    coating said gas-pervious package with plastic or elastomer on the side facing the pressure-sensitive coating of said backing element only in those areas where said package contacts said adhesive bandage, and in the seal areas immediately adjacent the peripheral portions of said package;
    sterilizing said adhesive bandage subsequent to sealing said package by exposing the sealed package to gas or steam which is allowed to penetrate into said package and the unsealed areas of said package surrounding said adhesive bandage.

12. The method in accordance with claim 10 wherein the sealing together of the peripheral portions of internal surfaces of said package is accomplished by a method utilizing heat, pressure or ultrasonics, either singly or in combination.

* * * * *